United States Patent [19]

Frezza

[11] Patent Number: 5,779,677
[45] Date of Patent: Jul. 14, 1998

[54] AUTOMATIC DRUG INJECTOR

[75] Inventor: Pierre Frezza, Charly, France

[73] Assignee: Laboratoire Aguettant, Lyons, France

[21] Appl. No.: 669,444

[22] PCT Filed: Jan. 16, 1995

[86] PCT No.: PCT/FR95/00047

§ 371 Date: Aug. 1, 1996

§ 102(e) Date: Aug. 1, 1996

[87] PCT Pub. No.: WO95/19194

PCT Pub. Date: Jul. 20, 1995

[30] Foreign Application Priority Data

Jan. 17, 1994 [FR] France ................... 94 00608

[51] Int. Cl.⁶ ........................................ A61M 5/20
[52] U.S. Cl. ................. 604/134; 604/135; 604/131
[58] Field of Search ..................... 604/131, 134, 604/135, 136, 137, 138, 139, 156, 157

[56] References Cited

U.S. PATENT DOCUMENTS

| 4,258,713 | 3/1981 | Wardlaw | 604/139 |
|---|---|---|---|
| 4,661,098 | 4/1987 | Bekkering | 604/135 |
| 4,676,781 | 6/1987 | Phillips | 604/135 |
| 4,717,383 | 1/1988 | Phillips | 604/135 |
| 5,114,406 | 5/1992 | Gabriel | 604/136 |
| 5,137,516 | 8/1992 | Rand et al. | |
| 5,176,643 | 1/1993 | Kramer | 604/135 |
| 5,300,030 | 4/1994 | Crossman | 604/134 |
| 5,358,489 | 10/1994 | Wyrick | 604/135 |

FOREIGN PATENT DOCUMENTS

| 649068 | 2/1992 | Australia | 604/131 |
|---|---|---|---|
| 0516473 | 12/1992 | European Pat. Off. | |
| 562671 | 3/1993 | European Pat. Off. | 604/156 |
| 2342079 | 9/1977 | France | 604/137 |
| 2654938 | 5/1991 | France | |
| WO 92/18187 | 10/1992 | WIPO | |
| WO 92/20388 | 11/1992 | WIPO | |
| 9313819 | 7/1993 | WIPO | 604/157 |

*Primary Examiner*—Sam Rimell
*Assistant Examiner*—Luke J. Yeh
*Attorney, Agent, or Firm*—Oliff & Berridge, P.L.C.

[57] ABSTRACT

The injector has a reservoir containing a drug. The injector has a tubular body with a tubular wall, a plunger, a needle and a plunger rod. The tubular body also has two springs. The first spring is compressed from bearing on a part of the inner surface of the tubular body and on a piece that is connected to the plunger rod. The first spring pushes in the direction in which the needle protrudes. The second spring acts in the opposite direction of the first spring. The second spring is compressed by bearing on a part of the inner surface of the injector body and on a ring. The force exerted by the second spring is greater than that exerted by the first spring. The ring is slidably mounted and is capable of entraining the reservoir in the direction of the retraction of the needle. The ring is blocked by a movable abutment. The plunger rod cooperates with the movable abutment to release the second spring and cause the retraction of the needle.

9 Claims, 4 Drawing Sheets

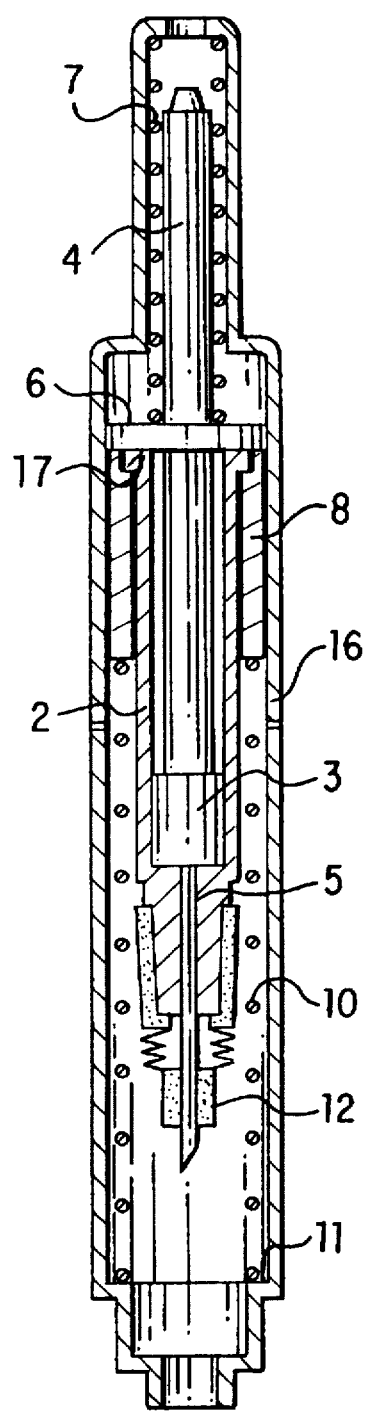
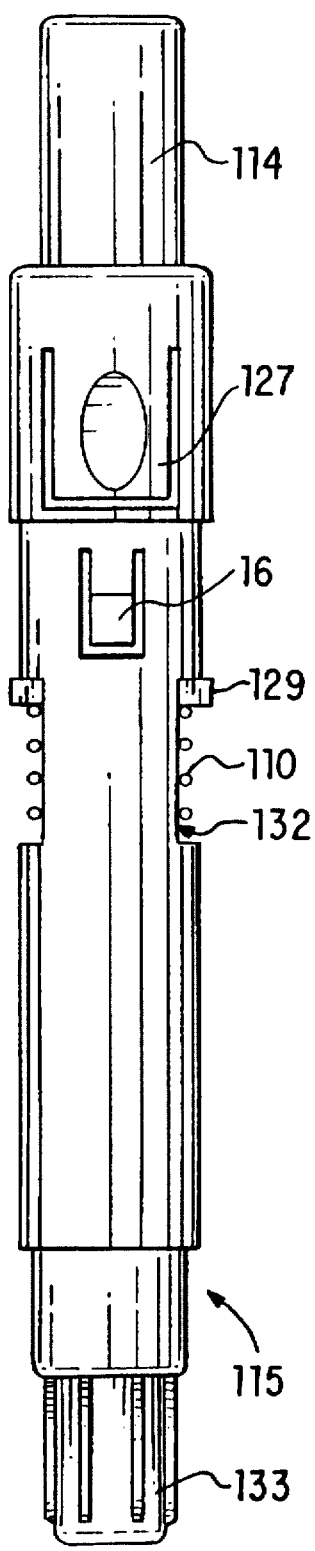
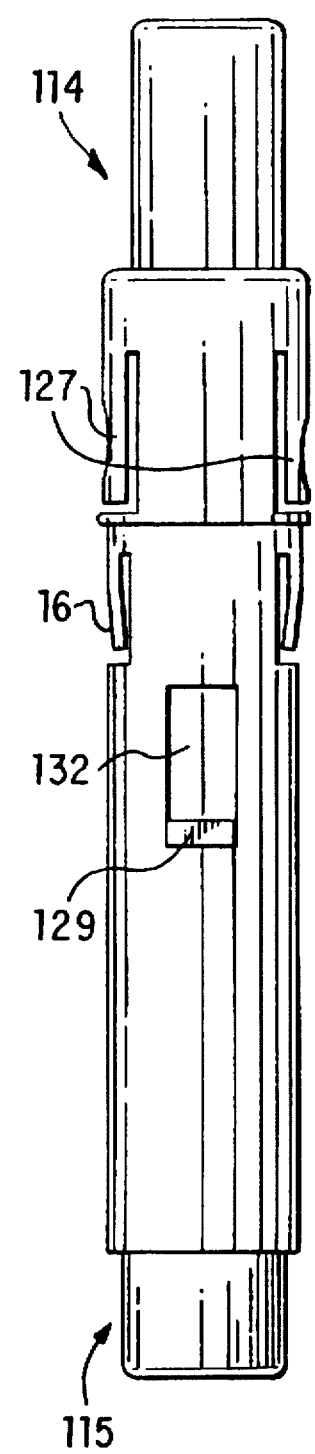
FIG. 4
FIG. 5
FIG. 6

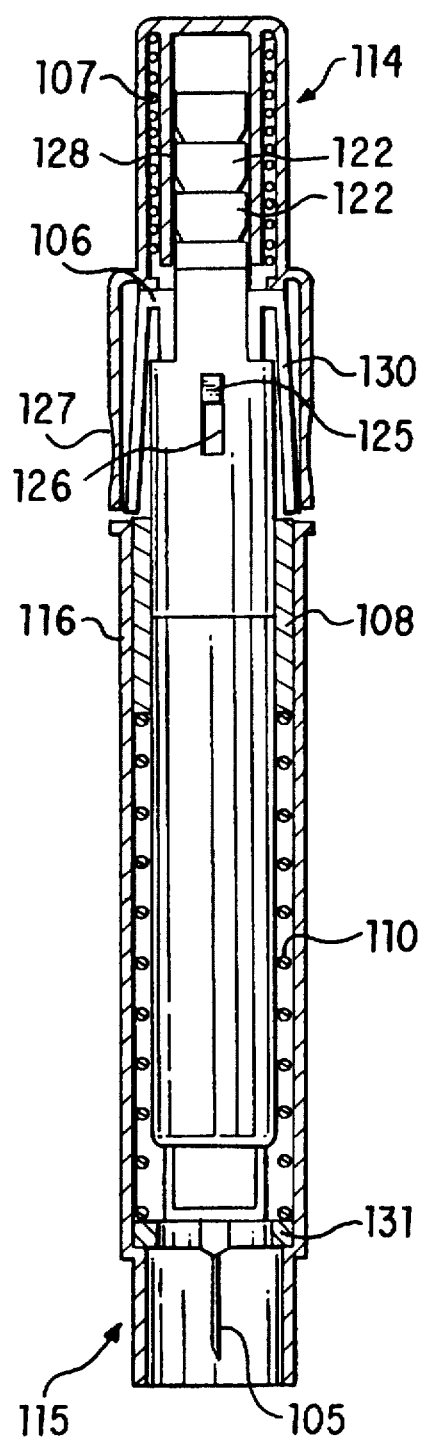
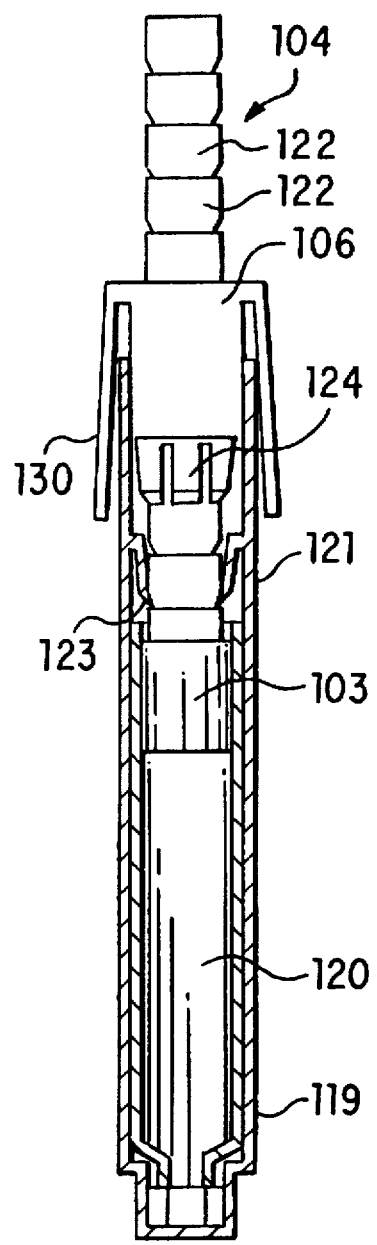
FIG. 10
FIG. 11

AUTOMATIC DRUG INJECTOR

BACKGROUND OF THE INVENTION

The invention relates to an automatic drug injector. Such an injector allows a liquid drug to be introduced into a patient's body through his skin. To do this, a hollow needle pierces the patient's skin, penetrates to a defined depth inside the patient's body, then, with the aid of a plunger, the liquid drug is injected, from an ampoule or from the body of a syringe, through the needle and into the patient's body.

With injectors of this kind, a person who is not accustomed to performing injections may nevertheless do so. For this, it suffices to place the injector on the patient's skin and to trigger the mechanism. It is even possible to inject oneself with a drug, without the intervention of a doctor or a nurse. Thus, it is no longer necessary to prolong the hospitalization of an individual for the sole reason that this individual has to take injections of drugs several times a day.

It is preferable that the person who receives the drug should not see the needle, especially if he is giving himself the injection. It is thus easier for him to overcome his fear of the pricking.

For reasons of safety, it is preferable for the needle to be protected following the injection. It is possible simply to protect it with a cap, or else to retract it from the injector and place it in a rigid case. However, it is advantageous that the needle retract automatically, without manual intervention, in order to achieve maximum safety. Indeed, if the patient is a virus carrier, there is a high risk of the needle being contaminated following the injection, and if someone injures himself with this needle, the disease (AIDS, hepatitis B, etc.) carried by the virus may be transmitted.

The document WO 92/20388 discloses an automatic injector of this type in which the needle does not retract automatically at the end of the injection. There is therefore a risk of contamination with such an injector once it has been used.

A syringe is also known, from the document WO 92/18187, in which the needle retracts automatically in the plunger rod when the plunger has arrived at the end of its stroke. This syringe can be used only once. Moreover, only the retraction of the needle is automatic. The pricking and the injection are effected manually.

Patent FR 2 342 079 for its part discloses an injector in which the three operations—pricking, injection, retraction—are effected automatically. The disadvantage of this device is that it is necessary, on the one hand, to release a first spring in order to activate the pricking and the injection, and, on the other hand, when these two operations have been effected, to activate the retraction of the needle by releasing another spring. Once the injection has been carried out, it is possible to retract the needle from the patient's body without activating the retraction of the needle to inside the body of the injector. The needle may therefore find itself unprotected following the injection, and there is therefore a risk of contamination.

SUMMARY OF THE INVENTION

This injector comprises in particular a cylindrical body in which the body of a syringe slides axially, and also three springs. One spring activates the introduction of the needle into the patient's body, another the injection of the drug, and the third the retraction of the syringe, with the needle, into the cylindrical body.

The object of the invention is to propose a device which is capable of injecting one or more doses of drug, is very simple to manipulate, and allows an operator who does not know how to perform injections to inject a drug dose, optionally into himself, while preventing any risk of accidental pricking following the use of the device. Another object is to make available an injector which is simple to produce and has a fairly low cost price.

To this end, the injector which the invention proposes is an automatic injector for a drug in liquid form, comprising:

a tubular body intended to be held by the user, a reservoir, with one or more chambers, containing the drug which is to be injected and comprising a tubular wall in the axis of the body, a plunger forming a seal, closing one end of the said tubular wall, and displaceable towards the other end where there is a hollow needle through which the liquid passes, and comprising a plunger rod, two compressed springs storing the energy which is necessary for the automatic functioning of the injector, characterized in that the first spring at least partially surrounds the plunger rod and is compressed by bearing, on the one hand, on a part of the inner surface of the injector body, and, on the other hand, on a piece connected to the plunger rod of the reservoir, this first spring acting in the direction of protrusion of the needle, in that the second spring, which acts in the opposite direction to the first spring, at least partially surrounds the tubular wall of the reservoir and is compressed by bearing, on the one hand, on a part of the inner surface of the injector body, and, on the other hand, on a ring which is mounted so as to slide along the outer surface of the reservoir and which is capable of entraining the reservoir in the direction of retraction of the needle, and which can be blocked in translation by means which include at least one movable abutment which is stressed elastically towards the inside of the injector body in the rest position, and against which the ring comes into abutment when it is in the rest position, in that the force exerted by the second compressed spring is greater than the force exerted by the first spring, and in that the piece which is connected to the plunger rod of the reservoir, and on which the first spring bears, cooperates, at the end of the plunger stroke, with the means for blocking the ring in order to release the second spring and cause the reservoir to ascend and the needle to retract inside the injector body.

Thus, it suffices to release the first spring so that, in succession, the needle emerges from the tubular body and penetrates into the body of the patient, the liquid is injected via the needle, and the needle retracts automatically, since it is the end of the injection stroke which activates the release of the second spring.

In addition, very few pieces are necessary for producing such an injector: a reservoir, a needle, a plunger with its plunger rod, a piece connected to the plunger rod and able to form, together with the latter, a monobloc piece, two springs, a ring, a tubular body and means for blocking the ring. To ensure the seal and sterility of the needle, at least one cap is necessary, but it has no other technical function.

In order to limit still further the number of pieces constituting the injector and in so doing to reduce its cost price, the means for blocking the ring will advantageously be made integral with the tubular body. In this case, the means for blocking the ring comprise at least one tongue cut out from the tubular body or attached to the inside thereof, and connected to the latter via its edge situated remote from the needle, and folded towards the inside of the tubular body.

Such an injector can be designed to inject a single dose of drug, or else several.

In the former case, namely that of a single-dose injector, given the low cost price of the device, the latter is disposable. In one embodiment, the plunger rod includes a narrowed zone which snaps into the annular bottom of the tubular body of the injector, thereby blocking the plunger in translation, and the injection is triggered by the rupture of that end of the plunger rod projecting from the tubular body.

The act of breaking the plunger rod is a guarantee of inviolability of the injector and proves to the user that the injector he is using is new and has never been utilized.

In this embodiment, that end of the reservoir situated remote from the needle advantageously includes an outer rim capable of passing freely between the tongues of the injector body, without modifying the position of these, and of bearing against a shoulder formed at that end of the ring opposite the end which the second spring bears against, and the piece connected to the plunger rod has a diameter at least equal to the external diameter of the ring and is positioned on the plunger rod in such a way that, at the end of the stroke, it is disposed in proximity to the ring and has spaced apart the tongues blocking the latter.

If the end of the needle is protected, prior to injection, by a pierceable cap mounted with a force fit on the reservoir and comprising a very fine and deformable lateral wall, it is unnecessary to remove this cap before proceeding with the injection. However, for greater guarantee of the bacteriological seal, it is preferable to provide a second and more rigid cap obturating the lower opening of the tubular body, through which opening the needle emerges.

In the case where the injector can inject several doses of drug, a dosing device is combined with the injector. In this dosing device of a known type, the plunger rod thus comprises a plurality of successive and annular catches, uniformly spaced along the axis of the tubular body, over a length which is at least equal to the plunger stroke necessary for emptying the reservoir, each catch having a cross-section which decreases in the direction of the plunger. The tubular wall of the reservoir, and the piece connected to the plunger rod, include at least one elastic tooth which is adapted for penetration between two successive catches of the plunger rod and cooperates with these catches. According to the invention, the piece connected to the plunger rod allows the plunger to be blocked in translation vis-a-vis the tubular body by means comprising at least one abutment on the tubular body, against which abutment there comes to bear a movable part, elastically stressed in the rest position, of the piece connected to the plunger rod, and at least one part of the ring, which slides along the outer wall of the reservoir and on which the second spring bears, protrudes, through a slot, out of the tubular body of the injector, making it possible to return the relaxed second spring manually to its initial compressed and blocked position.

In this variant, the means for blocking the piece connected to the plunger rod advantageously comprise at least one first tongue which, forming the piece connected to the plunger rod, is made integral with the latter via its edge situated remote from the needle and is inclined from the inside outwards, in such a way that in the rest position its edge situated beside the needle comes to bear against an abutment integral with the tubular body, and at least one second tongue, cut out from the tubular body and connected to the latter via its edge situated remote from the needle, faces a first tongue of the piece connected to the plunger rod, so as to be able to let this first tongue escape from its abutment by bearing on the second tongue of the tubular body. As before, this makes it possible to reduce the number of pieces, to facilitate the construction of the device, and to reduce the cost price of the assembly.

In order to limit the plunger stroke and to obtain a precise dosing of the quantity of drug injected, the piece connected to the plunger rod comprises at least one stud projecting into an axial slot which is formed in the tubular wall of the reservoir, and whose length is at least equal to the length of the stud, increased by the distance separating two catches of the plunger rod.

In this embodiment, the tongues constituting the piece connected to the plunger rod advantageously come to bear, at the end of injection of a dose, against that end of the ring opposite the end serving as a bearing for the second spring, and they space apart the tongues blocking the ring.

BRIEF DESCRIPTION OF THE DRAWINGS

The invention will at any rate be clearly understood from the description which follows and in which reference is made to the attached diagrammatic drawing which represents, by way of non-limiting examples, two embodiments of this device.

FIGS. 1 to 4 represent a first embodiment thereof.

FIG. 1 is a longitudinal cross-section of the device, in the storage position,

FIG. 2 is a longitudinal cross-section thereof, when the needle penetrates into the body of the patient, FIG. 3 is a longitudinal cross-section thereof, at the end of the injection, before the retraction of the needle, FIG. 4 is a longitudinal cross-section thereof, after the retraction of the needle.

FIGS. 5 to 11 represent a second embodiment.

FIG. 5 is a side view thereof, in the storage position,

FIG. 6 is a view thereof from another side, in the primed position,

FIG. 7 is a longitudinal cross-section thereof, in the primed position,

FIG. 8 is a longitudinal cross-section thereof, when the needle penetrates into the body of the patient, FIG. 9 is a longitudinal cross-section thereof, during the injection, FIG. 10 is a longitudinal cross-section thereof, at the end of the injection, when the needle is retracted, FIG. 11 is a cross-section of the reservoir of the injector.

Figure 1:
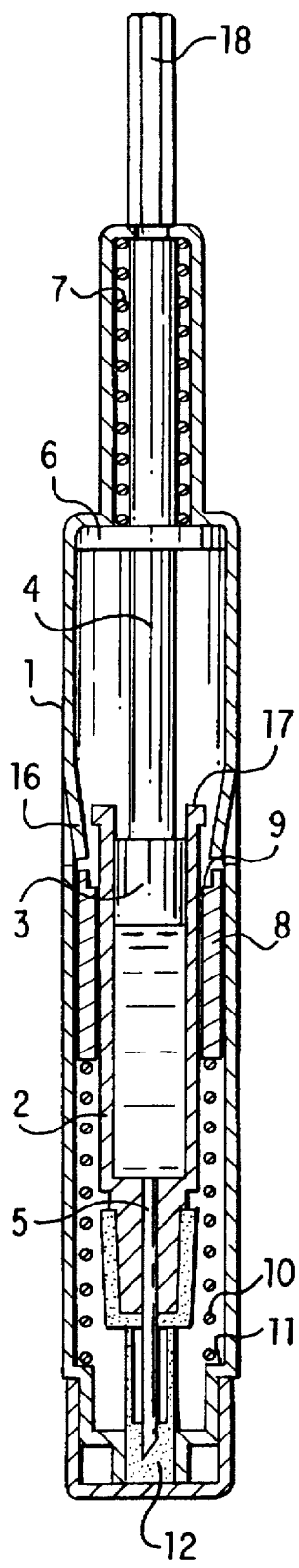
Figure 2:
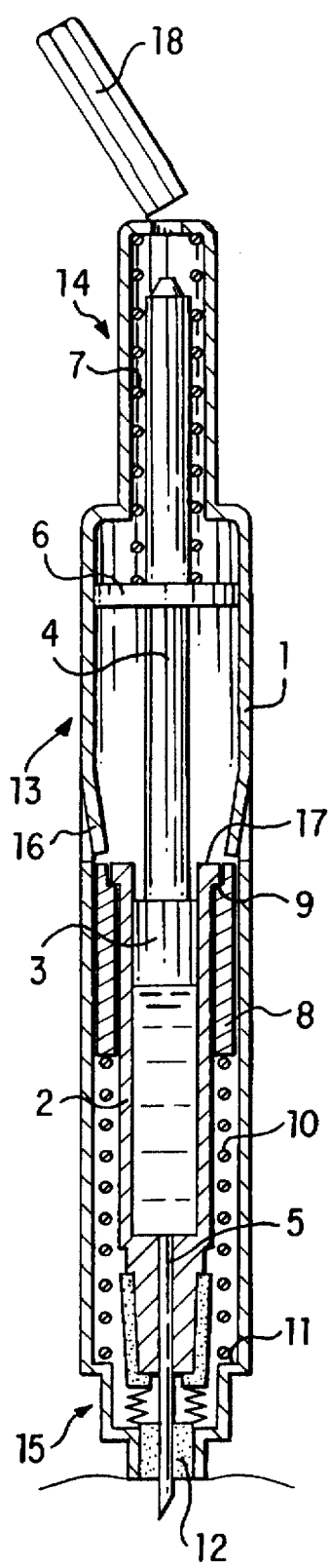
Figure 3:
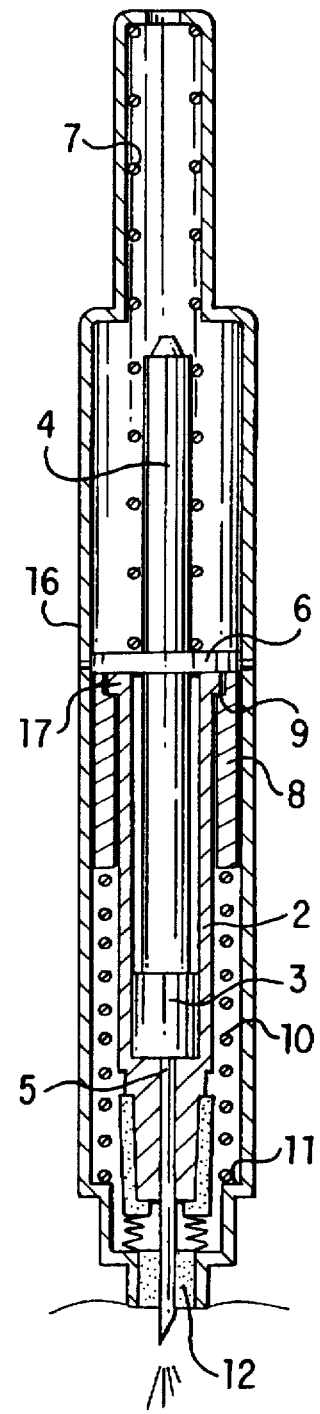

The automatic drug injector represented in FIGS. 1 to 4 is a disposable injector intended to effect only a single injection.

DETAILED DESCRIPTION OF THE PREFERRED EMBODIMENTS

This injector includes:

a tubular body 1 intended to be held by the user, a syringe comprising a tubular wall 2 in the axis of the body 1 made of glass or of plastic material, a plunger 3 made of elastomer and able to slide in the tubular wall 2 forming the body of the syringe, a plunger rod 4, and a hollow needle 5, a collar 6 connected to the plunger rod 4 and forming a monobloc assembly with the latter, a first spring 7 surrounding the plunger rod in the storage position (FIG. 1) and bearing, on the one hand, on the bottom of the tubular body 1, and, on the other hand, on the collar 6, a ring 8 equipped with a shoulder 9 and sliding along the outer surface of the tubular wall 2, a second spring 10 partially surrounding the tubular wall 2 of the syringe and bearing, on the one hand, on the ring 8, and, on the other hand, on a shoulder 11 of the tubular body 1, a cap 18 force-fitted on the lower end of the syringe body, and a second, rigid, cap closing the lower end of the tubular body 1.

The tubular body 1 is cylindrical. It is made up of a central part 13, an upper part 14 and a lower part 15. The upper part 14 has a diameter which is smaller than that of the central part. The lower part 15 is made up of two cylindrical parts of different diameters which are connected to each other, forming a shoulder, and connected to the central part 13, forming the shoulder 11. Two U-shaped cutouts are made in the central part 13, at an identical height, in two diametrally opposed positions, the base of the U being oriented towards the lower part 15 of the tubular body 1. These cutouts 19 form two tongues 16. The latter are folded towards the inside of the tubular body 1 and can space apart elastically from their folded position.

Inside this tubular body 1 there is a syringe 20. The hollow needle 5 of this syringe 20 is situated at the lower end of the body 1. The tubular wall 2 forming the body of the syringe 20 has an outer rim 17 at its upper end, that is the end remote from the needle 5. This outer rim 17 can pass freely between the tongues 16 of the injector body 1 without modifying the position of these tongues 16.

The drug to be injected is contained in the body of the syringe 20. The upper end of the body is closed by the elastomeric plunger 3. The other end is closed by a bottom on which the needle 5 is fixed. The cap 12 comprises a stopper in which the end of the needle is stuck, thereby ensuring the sealing of the needle. This stopper constitutes the bottom of the cylindrical cap 12 force-fitted on the lower end of the body of the syringe. The lateral wall 21 of this cap is very thin and deformable in such a way as to be able to fold in accordion fashion when it is stressed upon compression. This cap 12 is made, for example, of an elastomer, such as bromobutyl. The diameter of the stopper constituting the bottom of the cap 12 is substantially equal to the smallest internal diameter of the lower part 14 of the body 1.

The plunger rod 4 is connected to the plunger 3, by screwing for example. It extends towards the upper part 14 of the tubular body 1. The end 18 of the plunger rod 4 remote from the plunger 3 can be ruptured. The plunger rod 4 includes a narrowed zone 22 constituting the starting point for a rupture. This zone 22 is situated at the level of the upper end of the tubular body 1. The upper part 14 of this body 1 is equipped with a bottom drilled with a hole which has a diameter smaller than that of the plunger rod between the plunger 3 and the narrowed zone 22, and greater than the diameter of the rod 4 in the narrowed zone 22. Thus, as long as the end of the rod 4 is not broken, the plunger rod 4 is blocked in translation by the annular bottom of the tubular body 1.

The collar 6 is integral with the plunger rod 4. It is situated between the plunger 3 and the narrowed zone 22, at a distance from the narrowed zone 22 greater than or equal to the length of the upper part 14 of the body 1. Its diameter is just smaller than the internal diameter of the central part 13.

The spring 7, of internal diameter greater than that of the plunger rod 4 and of external diameter smaller than the internal diameter of the upper part 14, is compressed between the collar 6 and the annular bottom of the body 1 traversed by the rod 4.

The ring 8 is mounted slidably on the tubular wall 2 of the syringe. Its external diameter is smaller than or equal to that of the collar 6. The shoulder 9 is intended to cooperate with the rim 17 of the tubular wall 2.

The ring 8 is in abutment against the tongues 16. The other end of the ring is in contact with the spring 10 which bears, on the one hand, on the ring 8, and, on the other hand, on the shoulder 11 situated at the level of the connection between the central part 13 of the body 1 and its lower part 15.

The second cap closes the lower part 15 in order to perfect the bacteriological seal of the injector.

The functioning of this automatic injector for single use is as follows.

In the storage position represented in FIG. 1, the two springs 7 and 10 are compressed, the needle 5 is entirely inside the body 1, its end is protected by the cap 12, the lower end of the injector is covered by the second cap, and the ring 8 is in abutment against the tongues 16 under the action of the spring 10.

When it is desired to inject a patient with the drug contained in the syringe, it is necessary to operate as follows. The second cap is removed. The lower part 15 of the body 1 is then placed on the patient's skin, at the site where the drug is to be injected. It then suffices to break the end 18 of the plunger rod 4 (FIG. 2): the pricking, the injection, and the retraction of the needle are thus carried out automatically.

By breaking the end 18 of the plunger rod 4, the compressed spring 7 is released. Bearing on the bottom of the body 1, it pushes the collar 6. This force is then transmitted to the plunger 3. The needle 5 being stoppered, and the liquid drug being incompressible, the whole syringe is displaced. The stopper of the cap 12 is pierced by the needle 5, and the fine walls of this cap 12 fold in accordion fashion.

When the rim 17 of the syringe comes into abutment on the shoulder 9 of the ring 8, the descent of the syringe is stopped. The spring 7 still being compressed, it acts on the plunger 3 and injects the patient with the drug.

When the plunger 3 approaches the bottom of the syringe body, the collar 6 comes into contact with the tongues 16 which are folded towards the inside of the tubular body 1 and prevent the ring 8 from ascending. At the end of the injection (FIG. 3), the tongues 16 are completely spaced apart and no longer serve as an abutment for the ring 8. The force exerted by the spring 10 is markedly greater than the force exerted by the spring 7. The ring 8 thus ascends under the action of the spring 10, entraining with it the needle and the whole syringe, emptied of its contents.

The needle 5 withdraws from the patient's body and retracts inside the body 1. It is thus unnecessary, but nevertheless preferable, to put the second cap back in place, since there is no risk of injury with the needle. The injector can then be discarded without risk of contamination to third parties, since the needle is fully protected by the body 1.

FIGS. 5 to 11 represent a second embodiment of an injector according to the invention. In this embodiment, not all the drug contained in the injector is injected in a single injection. Only one dose of drug is injected per injection.

In this second embodiment, those elements having the same function as in the first embodiment are designated by the same reference numbers increased by 100.

The most important differences between the two embodiments are the manner of triggering the injection and the replacement of the syringe by a dosing device.

FIG. 11 represents a dosing device in longitudinal section, without the tubular body 101 of the injector.

This dosing device includes:

a capsule holder 119, a pre-filled glass capsule 120 accommodated in the capsule holder, a plunger 103 closing the capsule, a body 121 continuing the capsule holder 119, a plunger rod 104 connected to the plunger 103, for example by screwing, and a piece 106 mounted on the plunger rod 104.

The plunger rod 104 includes a plurality of successive and annular catches 122, uniformly spaced along the axis of the tubular body, over a length at least equal to the plunger stroke necessary for emptying the reservoir. The height of one catch is equal to the plunger stroke necessary for injecting one dose of drug. Each catch has a cross-section which decreases in the direction of the plunger 103.

The body 121 is fixed on the capsule holder 119. It has the same external diameter as the latter. On its inner wall it has eight elastic teeth 123 adapted, by virtue of their shape, for penetration between two successive catches 122 of the plunger rod 104. When the teeth 123 are between two catches 122, they prevent the plunger rod 104, and thus the plunger 103, from sliding in the direction tending to withdraw the plunger 103 from the capsule. The plunger 103 can then only push the liquid.

The piece 106 mounted on the plunger rod 104 also includes eight elastic teeth 124 adapted, by virtue of their shape, for penetration between two successive catches 122 of the plunger rod 104. When these teeth 124 are between two successive catches 122, these permit a relative movement between the piece 106 and the plunger 103, only in the direction in which these two pieces draw apart from one another. Furthermore, if a force is exerted on the piece 106 in the direction of the plunger 103 when the teeth are between two successive catches, this force is transmitted entirely by way of the rod 104 to the plunger 103.

The piece 106 also includes two studs 125 projecting inside a slot 126 formed in the body 121. These slots 126 have a length which is slightly greater than the length of the studs 125, increased by the distance separating two catches 122 of the plunger rod 104, in order to take account of the functioning play of the dosing device.

The piece 106 also includes two elastic tongues 130 extending along the body 121, on the outside of the latter, and slightly inclined in relation to the axis of the dosing device.

Such a dosing device is mounted in a tubular body 101. Like the tubular body 1 described hereinabove, the tubular body 101 includes a central part 113, an upper part 114 of diameter smaller than that of the central part 113, a lower part 115, two tongues 116, and a shoulder 111.

Two supplementary tongues 127 are formed in the body 101 proper. A U-shaped cutout 134 (as is shown in FIG. 5), the base of the U being oriented towards the lower part of the body 101, at two diametrically opposite sites, forms these tongues 127 which, in contrast to the tongues 116, are not folded towards the inside of the body 101.

A wall 128 formed in the upper part 114 of the body 101 is intended to separate the plunger rod 104 from a spring 107.

Two slots 132 are also provided in the body 101 in order to allow two studs 129 of a ring 108 to pass through. The ring 108 corresponds to the ring 8 of the first variant described. It differs from the ring 8 in that it has two diametrically opposite studs 129 and in that the shoulder 9 is rendered superfluous.

An elastic abutment 131 is mounted at the level of the shoulder 111 existing between the body 101 proper and its lower part 115. A spring 110 is compressed between this abutment 131 and the ring 108. The spring 107 is for its part compressed between the bottom of the upper part 114, which is not provided with an opening, and the piece 106.

A needle 105 is mounted on the lower part of the capsule 119. A cap 133 protects this.

The functioning of this injector is as follows.

In the storage position (FIG. 5), the spring 107 is compressed, the spring 110 is relaxed, the ring 108 is in the upper position, the studs 125 of the piece 106 connected to the plunger rod 104 are in abutment in the upper part of the slots 126, and the tongues 127 of the body 101 face the tongues 130 of the piece 106.

Figure 7:
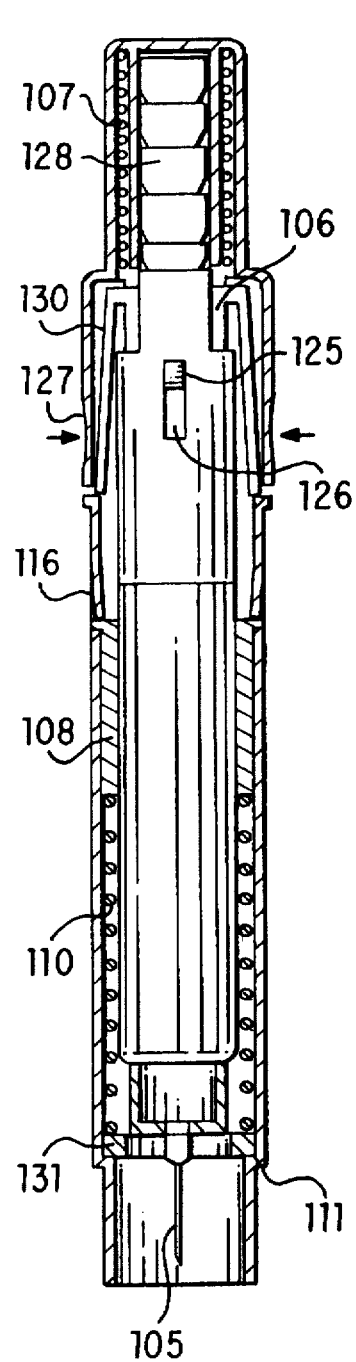

Before using the injector, it has to be primed. By virtue of the two studs 129 of the ring 108 which are guided in the slots 132, the ring 108 is lowered in the direction of the needle 105. It thus compresses the spring 110. When the upper part of the ring 108 is below the tongues 116, these fold towards the inside of the tubular body 101, in their rest position, and prevent the ring 108 from ascending, despite the thrust of the spring 110. The tongues 130 of the piece 106 connected to the plunger rod 104, which tongues rested on the ring 108, descend under the action of the spring 107. But they are stopped at the level of the U-shaped cutouts which are made to form the tongues 127 and which form an abutment (FIGS. 6 and 7).

It then suffices to remove the cap 133, and the device is ready to function.

Figure 8:
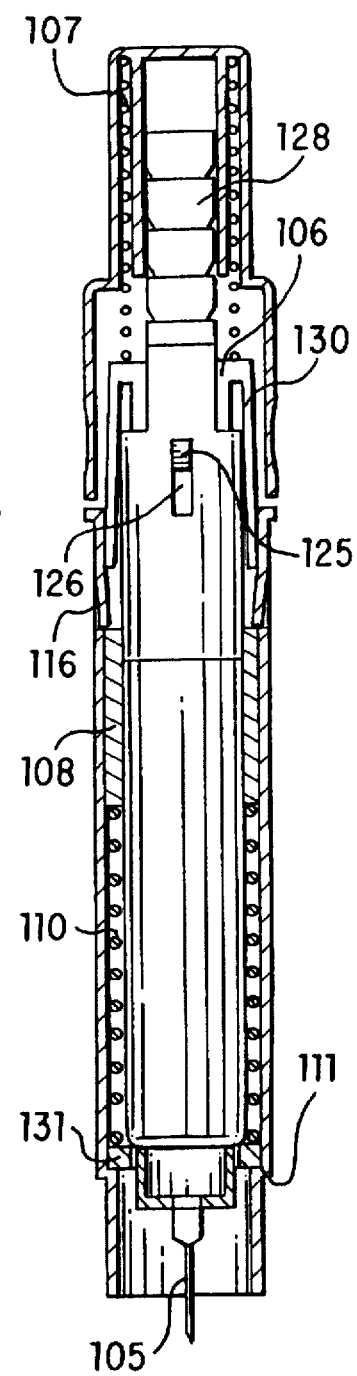
Figure 9:
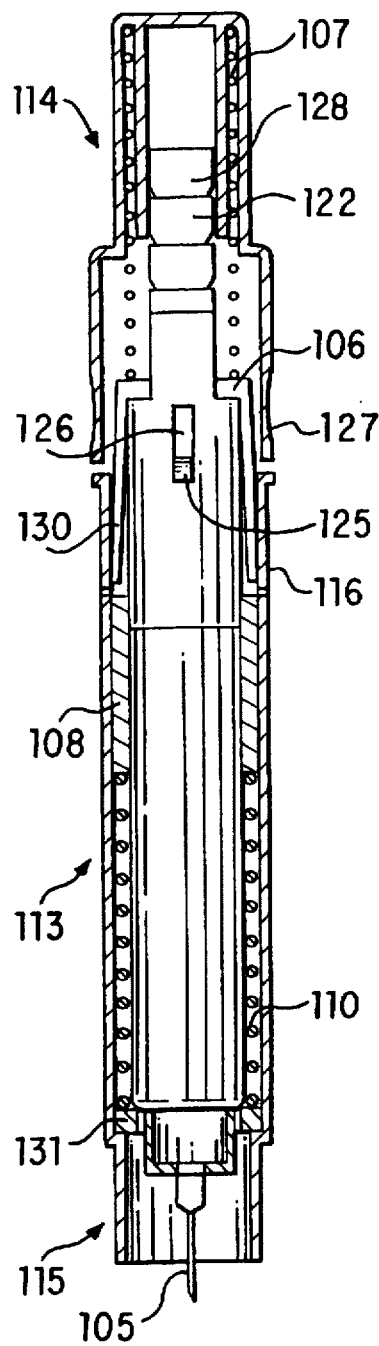

The front part of the injector is then placed on the zone to be pricked. To trigger the pricking, the injection, and the retraction of the dosing device, it suffices to press on the two flexible tongues 127 (FIG. 7). The latter then transmit the movement to the tongues 130 which, for this reason, escape from the abutment formed by the U-shaped cutouts. The spring 107 is then released and exerts a downwards force on the piece 106. The teeth 121 being between two successive catches of the plunger rod 104, this force is transmitted to the dosing device as a whole, by way of the plunger 103 and the incompressible liquid to be injected. The needle 105 then emerges from the device until the lower part of the capsule holder 119 comes to bear on the elastic abutment 131 (FIG. 8). The spring 107 then continues to exert a force on the piece 106. This force permits the injection of a dose of drug. The studs 125 are displaced in the slots 126. During the injection (FIG. 8), and especially shortly before the end thereof, the tongues 130 of the piece 106 spread apart the tongues 116 of the tubular body 101. At the moment when the studs 125 arrive in abutment in the slots 126, the tongues 116 are sufficiently spaced apart to release the ring 108 which is pushed by the spring 110. The force exerted by the latter is greater than that exerted by the spring 107. The ring 108 thus pushes the piece 106 upwards by way of the tongues 130. The force exerted by the spring 110 is sufficient to raise the dosing assembly and cause the piece 106 to slide from a catch 122 on the plunger rod 104. The studs 125 are then located in abutment in the upper part of the slots 126.

It then suffices to put the cap 133 back in place. The injector is in the storage position. Even if one omits to replace the cap 133, the needle 105 is protected inside the body 101 and there is no risk of injuring oneself on the needle. Indeed, the spring 110 being released and exerting a force greater than that of the spring 107, even an inadvertent action on the tongues 127 will have no effect on the dosing device and the needle, both of which will remain protected in the body 101.

It goes without saying that the invention is not limited to the embodiments described hereinabove by way of example, and instead it encompasses all the variants thereof.

Thus, for example, in another variant which has not been described, the syringe or the dosing device can be replaced by a syringe with several chambers. In a known manner, the various products contained in the chambers are then mixed before proceeding with the injection.

I claim:

1. An automatic liquid drug injector comprising:
   a tubular body;
   a reservoir having at least one chamber adapted for containing the drug, the reservoir positioned within the tubular body, the reservoir comprising:
   a tubular wall;
   a plunger sealing one end of the tubular wall and displaceable within the tubular wall towards the other end;
   a hollow needle positioned at the other end of the tubular wall; and
   a plunger rod connected to the plunger and extending out of the tubular wall;
   a ring slidably mounted on the tubular wall and adapted to entrain the reservoir in the direction of the needle;
   a first spring abutting at a first end against an inner surface of the tubular body and at a second end against the plunger rod, wherein the first spring biases the plunger rod in the direction of the needle;
   a second spring abutting at a first end against an inner surface of the tubular body and at a second end against the ring, wherein the second spring biases the ring away from the needle in a direction opposing the first spring, the second spring exerting a force greater than the first spring; and
   at least one movable abutment adapted to prevent the ring from translating in a direction away from the needle in the tubular body, wherein the plunger rod is adapted to move the at least one movable abutment to permit the ring to translate in a direction away from the needle in the tubular body.

2. The automatic injector of claim 1, further comprising an outer rim integral with the tubular wall at an end opposite the needle, wherein the outer rim is adapted to retain the ring on the tubular body, wherein the at least one movable abutment comprises at least one inwardly extending tongue on the tubular body, wherein the plunger rod comprises a collar adapted to move the tongue outward to allow the ring to translate in a direction away from the needle.

3. The automatic injector of claim 1, wherein the plunger rod extends through an end of the tubular body at a narrow zone of the plunger rod, wherein the narrow zone of the plunger rod is adapted to be broken to release the plunger rod to be translated by the first spring in the direction of the needle.

4. The automatic injector of claim 2, wherein the collar has an external diameter at least equal to the external diameter of the ring.

5. The automatic injector of claim 1, further comprising a pierceable cap enclosing the end of the needle, wherein the pierceable cap is attached at a first end to the tubular wall and sealing the tubular body at a second end, wherein the pierceable cap comprises collapsible walls intermediate between the first and second ends.

6. An automatic liquid drug injector comprising:
   a tubular body;
   a reservoir having at least one chamber containing the drug, the reservoir positioned within the tubular body, the reservoir comprising:
   a tubular wall;
   a plunger sealing one end of the tubular wall and displaceable within the tubular wall towards the other end;
   a hollow needle positioned at the other end of the tubular wall;
   a plunger rod connected to the plunger and extending out of the tubular wall, the plunger rod having a plurality of successive, uniformly spaced, annular catches;
   at least one elastic tooth extending inwardly from the tubular wall and adapted to engage a catch; and
   an annular piece concentrically positioned on the plunger rod and having at least one inwardly extending tooth adapted to engage a catch, wherein the annular piece has at least one outwardly extending elastic tongue;
   a ring slidably mounted on the tubular wall of the reservoir, wherein the ring has a tab extending through a slot in the tubular body;
   an abutment on the tubular body adapted to engage the at least one outwardly extending elastic tongue to prevent translation of the annular piece within the tubular body;
   a first spring abutting at a first end against an inner surface of the tubular body and at a second end against the annular piece, wherein the first spring biases the annular piece in the direction of the needle;
   a second spring abutting at a first end against an inner surface of the tubular body and at a second end against the ring, wherein the second spring biases the spring away from the needle in a direction opposing the first spring, the second spring exerting a force greater than the first spring; and
   at least one movable abutment adapted to prevent the ring from translating in the tubular body in a direction away from the needle, wherein the annular piece is adapted to move the at least one movable abutment to permit the ring to translate in a direction away from the needle in the tubular body.

7. The automatic injector of claim 6, further comprising at least one inwardly extending second elastic tongue in the tubular wall abutting the at least one outwardly extending elastic tongue of the annular piece, and adapted to release said at least one outwardly extending elastic tongue from said abutment on the tubular body for translation in a direction toward the needle.

8. The automatic injector of claim 6, further comprising a stud extending from the plunger rod into an axial slot in the tubular wall, wherein the length of the slot is equal to at least the length of the stud and two catches.

9. The automatic injector of claim 6, wherein the at least one outwardly extending elastic tongue is adapted to move the at least one movable abutment at the end of a dose.

* * * * *